United States Patent [19]

Walsdorf et al.

[11] Patent Number: 4,904,478

[45] Date of Patent: Feb. 27, 1990

[54] SLOW-RELEASE SODIUM FLUORIDE TABLET AND METHOD FOR TREATMENT OF OSTEOPOROSIS

[75] Inventors: Neill B. Walsdorf; Charles Y. C. Pak, Dallas, both of Tex.

[73] Assignees: Mission Pharmacal Company, San Antonio; Board of Regents, The University of Texas System, Austin, both of Tex.

[21] Appl. No.: 112,202

[22] Filed: Oct. 22, 1987

Related U.S. Application Data

[63] Continuation-in-part of Ser. No. 842,304, Mar. 21, 1986, Pat. No. 4,726,952, which is a continuation-in-part of Ser. No. 522,014, Aug. 11, 1983, abandoned.

[51] Int. Cl.$^4$ .......................... A61K 9/22; A61K 9/26
[52] U.S. Cl. ..................................... 424/468; 424/469; 424/470; 424/484; 424/502
[58] Field of Search ............... 424/468, 469, 470, 484, 424/502

[56] References Cited

U.S. PATENT DOCUMENTS

| | | | |
|---|---|---|---|
| 3,062,720 | 11/1962 | Costello | 167/82 |
| 3,402,240 | 9/1968 | Cain et al. | 424/22 |
| 3,577,514 | 5/1971 | Robinson | 424/22 |
| 3,653,914 | 4/1972 | Schmitt | 99/78 |
| 4,104,370 | 8/1978 | Bloch | 424/153 |
| 4,185,093 | 1/1980 | Carnes et al. | 424/153 |
| 4,405,596 | 9/1983 | Helbig et al. | 424/33 |
| 4,614,648 | 9/1986 | Bru | 424/44 |
| 4,726,952 | 2/1988 | Walsdorf et al. | 424/476 |

OTHER PUBLICATIONS

Reg. T.M. 1,300,132, Reg. 10/16/1984, Slow Fluoride, (Mission Pharmacal), (First Use in Commerce, Nov. 19, 1982).
Walsdorf, Aug. 14, 1985, Sworn Statement of Formula of Slo-Fluoride TM Tablet, Sodium Fluoride 25 mg., Carnauda Wax 100 mg., Talc 11 mg., Sugar 90 mg., Magnesium Stratate 4 mg.
Pak et al., J. Bone & Mineral Res., 1(6): 563-571, (1986).
Hasvold et al., "In Vitro Release and in Vivo Serum Fluoride Levels and Urinary Excretion After Different Sodium Fluoride Tablets", European Journal of Clinical Pharmacology, 1981, pp. 225-230.
Moller et al., "Massive Fluorosis of Bones and Ligaments", University's Roentgen Clinic, State Hospital, Copenhagen, 1932, pp. 269-294.
Farley et al., "Fluoride Directly Stimulates Proliferation and Alkaline Phosphatase Activity of Bone-Forming Cells", Science, vol. 222, pp. 330-332.
Jowset et al., "Effect of Combined Therapy with Sodium Fluoride, Vitamin D and Calcium in Osteoporosis", The American Journal of Medicine, vol. 53, Jul. 1972, pp. 43-49.
Pekkanen, "The Hidden Health Risk Most Women Face", Reader's Digest, Nov. 1985, pp. 72-77.
The Consensus Development Conference Statement, "Osteoporosis", Apr. 2-4, 1984.
Butz et al., "Influence of Alkaline Salts and Acetazoleamide on Urinary Excretion of Citrate and Oxalate in the Rat", Abstracts of the 5th Symposium on Experimental Urology, 1980.
Pak et al., "The Hypercalciurias Causes, Parathyroid Functions, and Diagnostic Criteria", The Journal of (List continued on next page.)

*Primary Examiner*—Shep K. Rose
*Attorney, Agent, or Firm*—Arnold, White & Durkee

[57] ABSTRACT

A novel slow-release sodium fluoride preparation and its use. Such slow-release sodium preparation comprises carnauba wax and talc and may be used to provide a safe but effective level of fluoride in serum, optimal for the treatment of osteoporosis. Gastrointestinal side effects are minimized by limiting the amount of fluoride released in the stomach and rheumatic complications are reduced by avoiding toxic levels of fluoride is serum. The amount of fluoride absorbed is nevertheless sufficient to stimulate bone formation and prevent fractures. Thus, the maintenance of serum fluoride as encompassed in this invention, allows for a safe and effective treatment of osteoporosis.

23 Claims, 5 Drawing Sheets

OTHER PUBLICATIONS

Clinical Investigation, vol. 54, Aug. 1974, pp. 387–400.
Bishop, "America's New Hunger for Calcium Presents a Nutritional Dilemma", The Wall Street Journal, 1986.
Christiansen et al., "Does Calcium Treatment Prevent Postmenopausal Bone Loss? A Double-Blind Controlled Clinical Trail", Journal of Bone and Mineral Research, 1:166A, 1986.
Matkovic et al., "Influence of Calcium on Peak Bone Mass: A Pilot Study", Journal of Bone and Mineral Research, 1:166A, 1986.
Riggs et al., "In Women Dietary Calcium Intake and Rates of Bone Loss from Midradius and Lumbar Spine Are Not Related", Journal of Bone and Mineral Research, 1:166A, 1986.
Skillman, M.D., "Management for all Women, Prevention for Some", Consultant, Feb. 1984, pp. 153–165.
Belizan M.D. et al., "Reduction of Blood Pressure with Calcium Supplementation in Young Adults", JAMA, Mar. 4, 1983, vol. 249, No. 9, pp. 1161–1165.
Riggs et al., "Effect of the Fluoride/Calcium Regimen on Vertebral Fracture Occurrence in Postmenopausal Osteoporosis", The New England Journal of Medicine, Feb. 25, 1982, pp. 446–450.
Nordin et al., "Treatment of Spinal Osteoporosis in Postmenopausal Women", British Medical Journal, Feb. 16, 1980, pp. 451–454.
Heaney et al., "Menopausal Changes in Calcium Balance Performance", J. Lab. Clin. Med., Dec. 1978, pp. 953–963.
Recker et al., "Efforts of Estrogens and Calcium Carbonate on Bone Loss in Postmenipausal Women", Annals of Internal Medicine, vol. 87, No. 6, Dec. 1977, pp. 649–655.

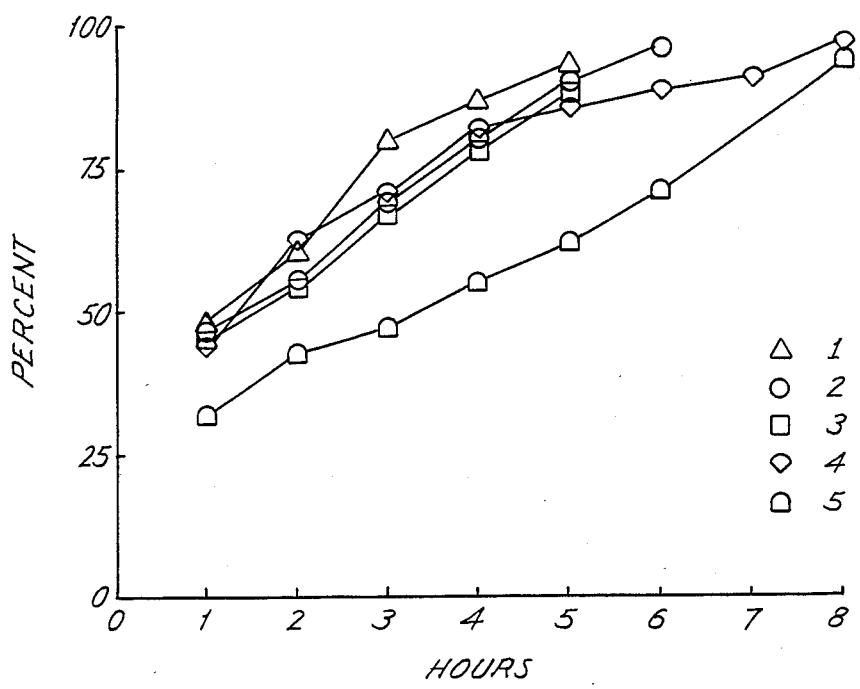
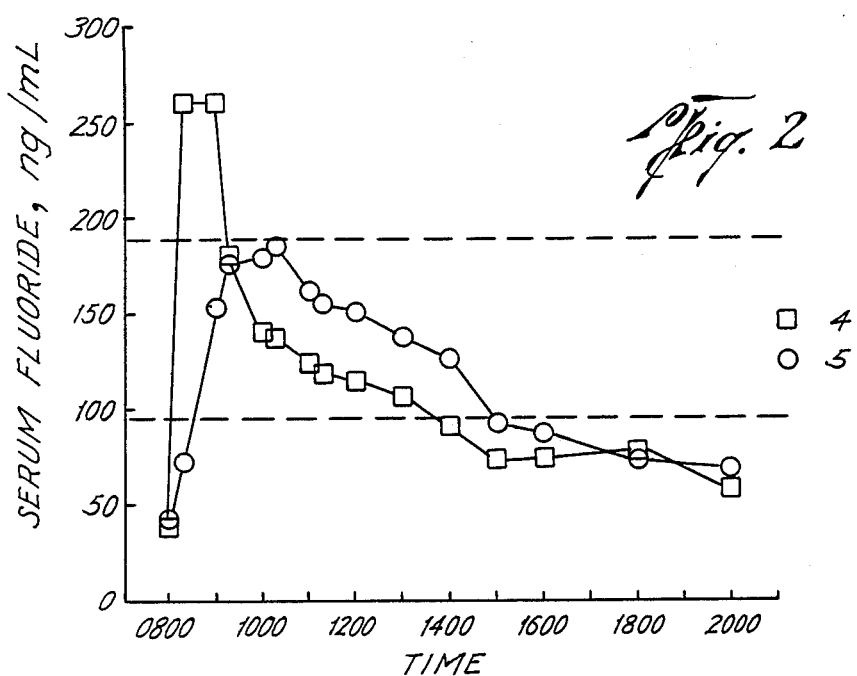

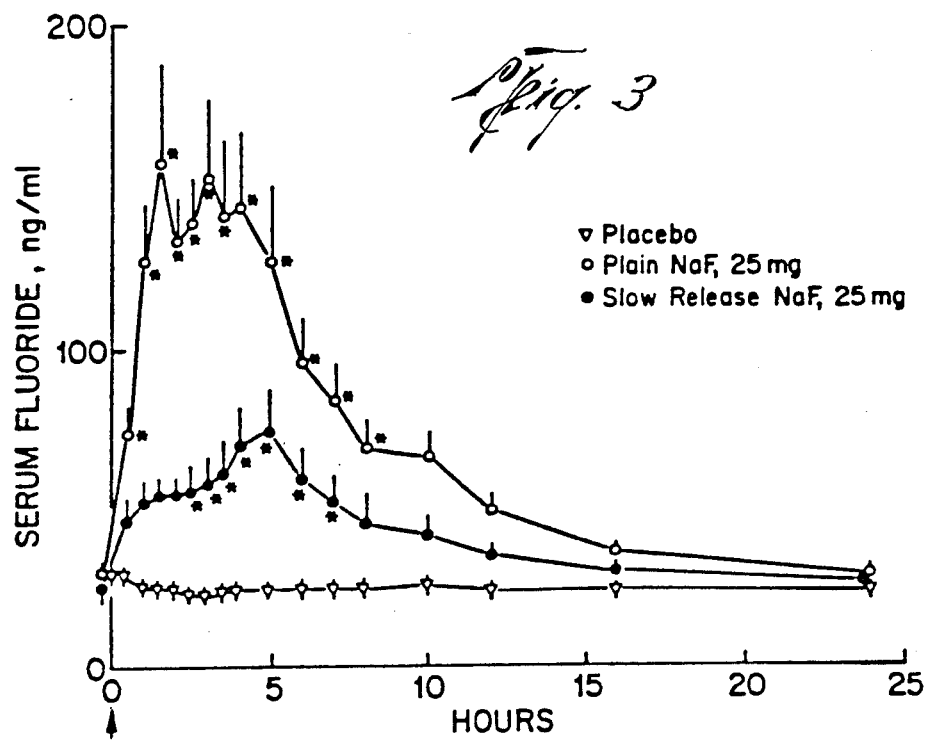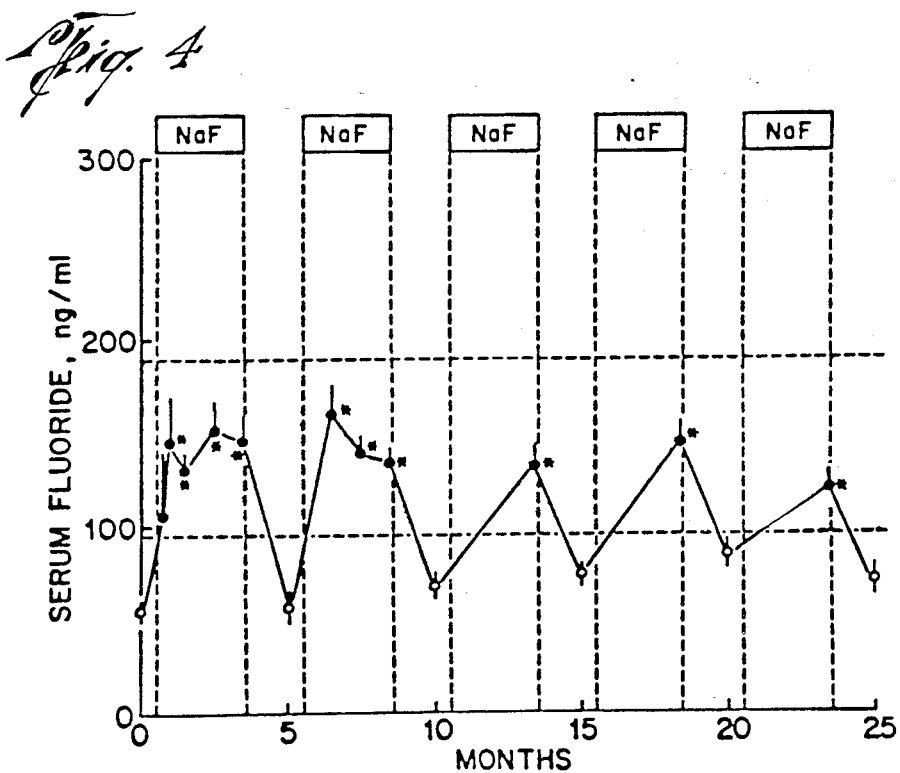

SLOW-RELEASE SODIUM FLUORIDE TABLET AND METHOD FOR TREATMENT OF OSTEOPOROSIS

Developmental work relating to part of the present invention was supported by grants from the United States government National Institutes of Health (POI-AM 20543 and ROI-AM 16061).

This application is a continuation-in-part of Ser. No. 842,304, filed on Mar. 21, 1986, now U.S. Pat. No. 4,726,952, which is a continuation-in-part of the then co-pending application Ser. No. 06/522,014 filed on Aug. 11, 1983 and since abandoned.

BACKGROUND OF THE INVENTION

Osteoporosis is a common disabling bone disease, particularly in post-menopausal women. Gradual loss of bone makes it porous and weak. Fracture of spine, hip and forearm frequently develop even without significant trauma.

Once the osteoporotic disease has developed, so much bone mass may already have been lost such that treatments directed at preventing further bone loss (for example, calcium supplements) would likely be of limited value. An ideal goal of therapy in patients with established osteoporosis with fracture is to provide a treatment program that will increase bone mass and restore "lost" bone. Unfortunately, most available treatment programs have failed to augment bone mass (Pak, The Menopause, Edit. J. J. Buchsbaum Springer-Verlag, 1983, pp. 35–54).

Sodium fluoride may be one agent capable of making more bone in osteoporosis. This possibility was first recognized in 1932, when Moller and Gudjonsson noted skeletal sclerosis in subject with overexposure with cryolite rich in fluoride (Acta Radiol., Vol. 13, 1932, pp. 269–294). It is now known that fluoride causes proliferation and increases the activity of osteoblasts, cells responsible for bone formation (Farley et al., Science, Vol. 222, 1983, pp. 330–332). When fluoride alone is given to patients with osteoporosis, the newly-formed bone is poorly mineralized (that is, deficient in calcium phosphate). However, when adequate calcium supplementation is provided along with fluoride, formation of mineralized bone may be stimulated (Jowsey et al., Amer. J. Med., Vol. 53, 1972, pp. 43–49). Using sodium fluoride (50–60 mg/day) with calcium supplement (800–1500 mg elemental calcium/day), formation of new bone has been shown on actual microscopic examination of biopsied bone (Briancon and Meunier, Orthop. Clin. North Amer., Vol. 12, 1998, pp. 629–648). Moreover, the rate of bone fracture was shown to be significantly reduced by treatment, compared to that of the untreated group (Riggs et al., N. Engl. J. Med., Vol. 306, 1982, pp. 446–450). Thus, there are sufficient references to suggest that long-term treatment with sodium fluoride could be effective in treating established osteoporosis.

Unfortunately, sodium fluoride has been associated with frequent adverse reactions. In several long-term trials, gastrointestinal side-effects (nausea, vomiting, diarrhea, bleeding) occurred in 16–50% of patients and rheumatic complications (painful foot and knee due to synovitis and plantar fascial syndrome) occurred in 17–32% (Table 1).

TABLE 1

| Side Effects of Conventional Sodium Fluoride | | |
|---|---|---|
| Side Effects | Authors | Percentage of Patients |
| Gastrointestinal | Riggs et al. (1980) | 19.4 |
| | Riggs et al. (1982) | 16.4 |
| | Briancon and Meunier (1981) | 21.5 |
| | von Kesteren et al. | 50.0 |
| Rheumatic | Riggs et al. (1980) | 30.6 |
| | Riggs et al. (1982) | 23.0 |
| | Briancon and Meunier (1981) | 32.4 |
| | Franke et al. (1974) | 17.4 |

These complications have precluded the widespread acceptance of sodium fluoride for the treatment of osteoporosis. It should be noted that the above clinical trials were conducted with plain or acid resistant form of sodium fluoride. As will be shown in the embodiments of the present invention, rapid release of fluoride could have caused these complications. Sufficient amount of fluoride would have been released into the gastric juice to cause the formation of hydrofluoric acid, which could then have "corroded" gastric lining. Moreover, because of the rapid absorption of hydrofloric acid, a high level of fluoride in blood would have been reached to cause joint complications.

A slow-release form of sodium fluoride could potentially avert or minimize these complications. However, to the best of our knowledge, an effective slow-release form of sodium fluoride, as embodied in the present invention, has never been used for the long-term treatment of osteoporosis.

In a study published in the European Journal of Clinical Pharmacology, entitled "Pharmacokinetics of Fluoride in Man after Single and Multiple Oral Doses, conducted by Ekstrand, et al. (Europ. J. Clin. Pharmacol., 12:311 (1977)), subjects were studied with multiple dosing with rapid-release sodium fluoride tablets in four experiments, in each after a 12 hour fast, and also fifteen single dose experiments were conducted. It was shown that sodium fluoride as capsules or non-slow-release tablets may cause a rapid rise in serum fluoride, from 19 ug per liter to as high as 400 ug per liter within one hour when given orally as a single dose.

The Hasvold and Ekren reference (*Eur. J. Clin. Pharmacol*, 19:525 (1981)) describes the use of: (1) rapid-release sodium fluoride tablets; (2) the use of enteric coated sodium fluoride tablets which are resistant to gastric but not intestinal dissolution; and (3) the use of "sustained release" sodium fluoride tablets of undisclosed composition. The experiments reported in the Hasvold and Ekren reference examine blood levels of fluoride for only 12 hours following but a single oral dose of a supposed sustained release sodium fluoride tablet. As shown in Tables 3 and 4 of the Hasvold and Ekren reference, administration of a sustained release sodium fluoride (SR) tablet resulted in a serum fluoride peak being reached after only two hours. Additionally, this serum fluoride peak shown in the Hasvold and Ekren reference was in fact above the upper limit of the fluoride therapeutic WindoW (190 ng/ml or 10.0 micromolar). The Hasvold and Ekren reference describes a serum fluoride pattern after but a single treatment with a sustained release sodium fluoride tablet and would be likely to be toxic at a continued similar dosage. The in vivo serum fluoride levels resulting from the "sustained release" tablets of the Hasvold and Ekren reference are similar to those resulting from immediate release fluoride tablets insofar as the serum fluoride peak was within two hours and provided a potentially toxic level of sodium fluoride higher than the therapeutic window. The present invention describes a tablet usable in daily treatment to continually maintain serum sodium fluoride concentrations within a therapeutic window of 95 ng/ml to 190 ng/ml. The continued maintenance of serum fluoride levels within the therapeutic window is necessary, for example, for successful treatment of osteoporosis.

There is considerable evidence that a slow-release formulation of sodium fluoride would be desirable in the treatment of postmenopausal osteoporosis. As will be discussed under embodiments of the present invention, an effective slow-release sodium fluoride may obviate or alleviate gastrointestinal or rheumatic complications of rapid release preparations, maintain serum fluoride within the therapeutic window, augment spinal bone mass and inhibit fractures.

The tablet preparation of the present invention was sodium fluoride imbedded in wax matrix (carnauba wax). This continuation-in-part application includes a more clear definition of the discovery that an inclusion of a small amount of talc with the carnauba wax imparts or contributes to the sustained release characteristic, thus assuring favorable clinical effects observed in the treatment of osteoporosis.

Objects of the present invention include novel tablets, methods of making the tablets, and therapeutic uses of the tablets. The tablets of the present invention comprise sodium fluoride effective for the treatment of bone diseases such as osteoporosis. Therapeutic use of the tablets of the present invention precludes the major adverse patient reactions to fluoride normally heretofore experienced with the use of customary "rapid-release sodium fluoride preparations. Another object is to optimize a slow-release mechanism for an oral sodium fluoride tablet, particularly useful for the oral administration of sodium fluoride.

Embodiments of the present invention confer slow-release characteristics to oral sodium fluoride preparations which permit protection against above-mentioned side effects of earlier fluoride preparations, while providing sufficient fluoride absorption to confer beneficial effect on bone. Evidence for this characteristic is provided herein and illustrated by Examples to follow.

SUMMARY OF THE INVENTION

The present invention involves a tablet adapted for slow gastrointestinal release of fluoride. This tablet comprises talc and sodium fluoride dispersed substantially homogeneously throughout a carnauba wax matrix. The tablet preferably comprises 1% to 10% talc, 35% to 70% carnauba wax and 8% to 12% sodium fluoride. The tablet of the present invention may also comprise 20% to 65% compressible sugar and 1% to 5% of a lubricant such as magnesium stearate. A most preferred embodiment of the present tablet comprises about 5% talc, about 45% carnauba wax, about 2% magnesium stearate lubricant, about 40% compressible sugar and about 11% sodium fluoride. Each sodium fluoride tablet of the present invention should contain about 25 mg sodium fluoride for convenience of administrative dosage. The above percentages are expressions of weight which should total about 100% for any particular composition.

The present invention also involves a process for maintaining an individual's serum fluoride at a therapeutic level between about 95 ng/ml and about 190 ng/ml, the process comprising administering to the individual twice daily a tablet adapted for slow gastrointestinal release of fluoride, the tablet comprising talc, carnauba wax and sodium fluoride in substantially homogeneous dispersion. The tablets utilized in this process are embodiments of those described above and the preferred administration is, of course, by oral ingestion, most preferably of a tablet comprising about 25 mg NaF twice daily.

BRIEF DESCRIPTION OF THE DRAWINGS

FIG. 1 shows patterns of in vitro fluoride dissolution of preparations comprising sodium fluoride.

FIG. 2 shows serum fluoride levels after ingestion of the tablets of the present invention or talc-free analog thereof.

FIG. 3 shows the mean serum fluoride level of 8 normal volunteers after administration of slow-release sodium fluoride, rapid release (plain) sodium fluoride or placebo (Pak et al., Am. J. Bone Min. Res., Vol. 1, pp 563–571, 1986).

FIG. 4 shows the mean serum fluoride level of 41 patients with osteoporosis being administered slow-release sodium fluoride (Pak et al., Am. J. Bone Min. Res., Vol. 1, pp 563–571, (1986)).

PREFERRED EMBODIMENTS OF THE PRESENT INVENTION

Figure 5:
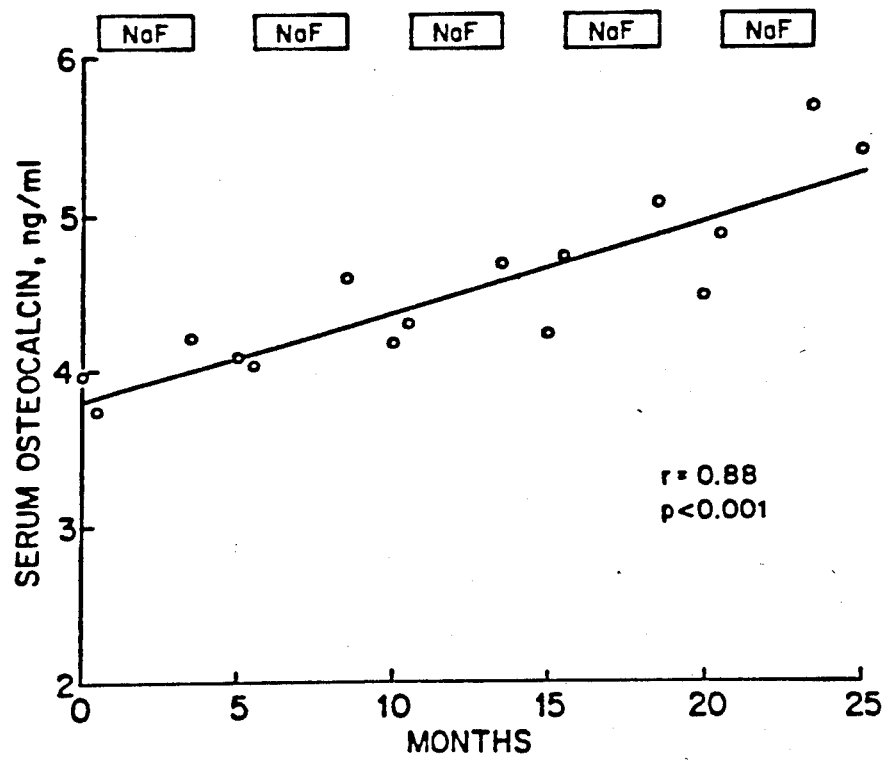
FIG. 5 shows serum osteocalcin level after slow-release NaF treatment.

The present invention includes a novel method for making a slow-release tablet preparation of sodium fluoride to be used for the treatment of osteoporosis. It was planned that, owing to its slow-release nature, this particular form of sodium fluoride would be safe to use and yet be therapeutically effective. On July 22, 1982, Dr. Charles Y. C. Pak, Professor of Medicine at the University of Texas Health Science Center at Dallas, obtained an investigational new drug status (IND 20,612) from the Food and Drug Administration for the study of this drug in osteoporosis. Since that time clinical studies with the slow-release sodium fluoride formulations of the present invention have been conducted. Results obtained in these studies as shown below, have now confirmed predictions of the parent patent application (USSN 06/522,014). The present application establishes more firmly the effective and safe use of slow-release sodium fluoride in the treatment of osteoporosis.

The slow-release sodium fluoride formulation of the present invention comprises a dose form, preferably a tablet, largely resistant to dissolution by gastric secretions but being gradually drained of sodium fluoride in an intestinal environment. The expectation that the specific formulation of the present invention providing slow-release fluoride would avoid adverse complications of sodium fluoride therapy was derived from our understanding of why these complications occur. The gastrointestinal side-effects are due to the corrosion of the intestinal lining (particularly of the stomach) by hydrofluoric acid (Eichler et al., Intern. J. Clin. Pharm., Vol. 20, 1982, pp. 334–338). The rheumatic complications result when fluoride is rapidly absorbed, allowing the blood concentration to reach the toxic level and causing acute skeletal fluorosis (formation of abnormal bone rich in fluoride near affected joints). The lower limit of the toxic level in serum has been set at 10 micromolar (uM) which is 190 nanogram (ng)/ml, since fluorosis has been reported above this concentration (Taves, Fed. Proc., Vol. 29, 1970, pp. 1185–1187).

From above considerations, it became apparent to us that oral sodium fluoride preparations which rapidly release fluoride would be particularly prone to cause adverse reactions. Sufficient amounts of hydrofluoric acid could form from the reaction of the released fluoride with the gastric hydrochloric acid to corrode the stomach lining. Moreover, since hydrofluoric acid is avidly absorbed in the stomach (Whitford and Pashley, Calc. Tiss. Intern., Vol. 36, 1984, pp. 302–307), fluoride absorption may be sufficiently rapid to allow the toxic limit in serum to be exceeded.

The conventional sodium fluoride preparations used in available long-term clinical trials were not slow-release preparations as in the present invention. They were plain preparations, enteric coated preparations or ineffective "sustained-release" preparations which, despite being sometimes administered with food or calcium supplements to reduce gastric irritation, probably caused sufficiently rapid fluoride release to cause the complications enumerated above.

The failure of others to produce effective slow-release preparations of sodium fluoride is probably due to the fear that insufficient amount of fluoride would be absorbed. The prior art would have taught so, since the slow-release preparation would limit the formation of hydrofluoric acid, recognized heretofore to be the predominant fluoride species which is absorbed from the intestinal tract (Whitford and Pahsley, Calc. Tiss. Intern., Vol. 36, 1984 pp. 302–307). Thus, using the customary dose of sodium fluoride (50 mg/day), the amount of fluoride absorbed was expected to be too low to exert a therapeutic effect on bone. It is believed that at least 5 micromolar or 95 ng/ml concentration of fluoride in serum must be reached to cause bone growth (Taves, Fed. Proc., Vol. 29, 1970, pp. 1 185–1187). The prior art would have taught that this therapeutic concentration would not have been reached using a slow-release preparation. The present slow-release sodium fluoride formulation is preferably a tablet resistant to gastric dissolution but being gradually drained of sodium fluoride in an intestinal environment.

The present invention involves controlled patient tests conducted using orally-administered tablets consisting of sodium fluoride dispersed substantially homogeneously throughout a matrix comprising talc and a major proportion by weight of carnauba wax, relative to total tablet weight or total unit-weight. The tablet is preferably compressed in a standard manner, resulting in a compact dense tablet in a compressed state.

However, for more optimal results, it has been determined that there is a novel preferred method of making said tablets which involves more than merely dispersal within the wax matrix. There is a unique combination of ingredients of the tablet of the present invention modified during the process of making. More particularly, prior to dispersion of sodium fluoride throughout the carnauba wax matrix, each of the sodium fluoride and the particles of wax will pass through a 14-mesh screen (U.S. Standard-Mesh) in order to disperse or remove any agglomerations and are milled or crushed, and after all ingredients are blended, the final blended product, prior to compacting into tablet form, will pass through a 12-mesh screen. Another preferred ingredient, magnesium stearate (NF) conventionally used in tablets for oral administration, is dispersed prior to blending by passage through a 20-mesh screen. Compressible sugar (NF) is a preferred conventional tablet ingredient (such as Nutab® or Destab®) and, prior to blending, is preferably passed through 14-mesh screen to eliminate any agglomerations. Another important was tablet ingredient is talc in minor amount. Although conventionally used as a "filler", talc has been shown to have a heretofore unrecognized, useful and critical function for effecting proper time-release of fluoride.

The preferred ingredients above-noted have broad ranges as follows: sodium fluoride at about 8 to abut 12 parts, a sugar at about 20 to about 65 parts, talc at about 1 to about 10 parts, magnesium stearate at about 1 to about 5 parts, substantially homogeneously dispersed throughout carnauba wax at about 35 to about 70 parts, on a weight basis of 100 parts by weight, preferably in a compacted tablet state. Preferred ranges are sodium fluoride at about 10 to about 12 parts, sugar at about 35 to about 45 parts, magnesium stearate at about 1 to about 3 parts, talc at about 4 to about 6 parts substantially homogeneously dispersed throughout carnauba wax at about 40 to about 50 parts, on a weight basis of !00 parts by weight.

The tablet-producing method of the present invention, broadly stated, includes passing sodium fluoride through a 14-mesh (U.S. Standard Mesh) screen, blending the screened alkali fluoride with talc (USP), passing carnauba wax and sugar (NF) through a 14-mesh screen and thereafter blending the screened carnauba wax and sugar with the blend of alkali fluoride and talc. Magnesium stearate, passed through a 20-mesh screen is thereafter blended with the blend of talc, sodium fluoride, carnauba wax and sugar to thereby obtain a substantially homogeneous dispersion. The homogeneous dispersion are passed through a 12-mesh screen, followed by a compacting and/or compressing of those final screened ingredients into a dense compacted tablet.

The size of tablets for oral administration may vary as a matter of convenience. For sodium fluoride tablets of the present invention, in treatment of bone diseases of patients, for convenience of dosage as well as with children and geriatric patients incapable of easily swallowing large tablets often, a typical range of tablet sizes is 25 mg., 50 mg., 100 mg., and the like.

While the present invention contemplates the use of some other wax having substantially comparable characteristics as that of carnauba wax, carnauba wax particularly with talc, is preferred as based on the success that has been achieved in its employment.

Carnauba wax, as noted above, has been previously utilized in pharmacy, most frequently, as the last stage in tablet coating. Skin sensitization by carnauba wax appears to be infrequent. The wax is a hard, high-polish wax not having any unpleasant odor upon melting. It has a melting point of 82–85.5 C. and a density of normally 0.990 to 0.999. Saponification value is 78 to 89. It is sparingly soluble in fat solvents at 25° C. and is quite soluable at 45° C. The hardness and the high-polish capability of this wax has been ascribed to the presence of esters of hydroxylated unsaturated fatty acids having about 12 carbon atoms. It is a hard greenish solid, of crystalline structure.

An example of a 230 mg tablet by weight of components, is:

| | |
|---|---|
| sodium fluoride USP | 25 mg. |
| carnauba wax, NF | 100 mg. |
| talc, USP | 11 mg. |
| magnesium stearate, NF | 4 mg. |
| compressible sugar (Destab), NF | 90 mg. |

This is given solely by way of example of typical but preferred weight ratios and ingredients for such a 230 mg. tablet, recognizing that, for example, minor adjustments such as of sodium fluoride to compressible sugar ratio may be made within the scope and breadth of the invention, ranges having been earlier defined in this specification.

It is within the scope and contemplation of the invention to include variations and modifications within ordinary skill, and to make substitution of equivalents obvious to those of skill in the art.

In preparation of tablets of the present invention, the following components in the formula described below were carefully milled, sized and blended together into a homogenous mixture:

TABLE 2

| Slow-Release Sodium Fluoride Tablets | |
|---|---|
| Component Material | Amount/Tablet |
| Sodium Fluoride U.S.P. | 25.0 mg |
| Carnauba Wax N.F. | 100.0 mg. |
| Talc N.F. | 11.0 mg. |
| Compressible Sugar N.F. | 90.0 mg. |
| Magnesium Stearate N.F. | 4.0 mg. |

In order to optimize a system which properly released the sodium fluoride over the prescribed period of time, a number of experiments with a number of substances were conducted. Because of the high level of adverse side effects experienced with ordinary preparations, desired slow-release system had to function without either "dose dumping" or lack of release from the matrix.

The present system involves a particular set of physical parameters in the manufacturing process to produce a tablet with precise and reproducible clinical effects. The specific use of carnauba wax, which has excellent high temperature release characteristics and exceptional physical hardness, is essential to maintain the architecture of the matrix and, more particularly, the retardant effect on the release rate of fluoride. The talc, in combination with the carnauba wax produces a slow but steady release of fluoride without "dose dumping." Talc performs an important function in creation of desired time-release characteristics.

A similar approach to this difficult problem with sodium fluoride in which a relatively toxic, irritating compound is released over a prolonged period and yet avoids the pitfalls of "dose dumping" and incomplete release has not been noted in known prior art. In efforts to produce a suitable method to approach this problem, a large number of "typical" waxes and "known" retardants were tested without useful results. As the clinical results indicate, the results achieved with the present formulation are not only theoretically effective, they are practical in a real clinical sense. Thus, the use of a unique combination of materials to produce a practical benefit or effect should be construed as invention.

When, in the composition shown in Table 2, carnauba wax was replaced by materials such as beeswax, Eudragit ® S-100 or cellulose acetate phthalate, the resultant sodium fluoride time-release characteristics were undesirable, e.g., too rapid and complete.

Clinical studies by the present inventors, using a slow-release formulation of sodium fluoride made according to specifications of this invention, have disclosed a surprising discovery. This discovery is that the use of this preparation at a customary dose of 50 mg/day is associated with minimum gastrointestinal and rheumatic complications, and yet provides sufficient fluoride absorption to keep the fasting serum fluoride level within the desired "therapeutic window" (above therapeutic threshold concentration 90 ng/ml but below the toxic concentration (190 ng/ml)). The slow-release sodium fluoride formulation of the present invention is adapted to gradually release sodium fluoride in the small intestine. Generally a 25 mg slow-release sodium fluoride formulation of the present invention gradually releases its sodium fluoride between about 1 and 25 hours after administration.

When 8 normal subjects were orally administered a single dose of slow-release sodium fluoride, the serum concentration of fluoride gradually rose, reaching a peak at 5–6 hours. Thereafter, the serum fluoride level gradually declined. The results suggested a slow but sustained absorption of fluoride, and indicated a discovery that fluoride may be absorbed as the anionic form in the intestine in lieu of the formation and absorption as hydrofluoric acid in the stomach.

Thirty-seven patients with osteoporosis were orally administered slow-release sodium fluoride at a dosage of 25 mg/twice/day orally (with crackers) intermittently (at 3-month intervals, separated by 2 months without treatment, repeated continuously). Fasting serum fluoride obtained during treatment was maintained within the therapeutic window (FIG. 4). Thus, serum fluoride on treatment was above the lower limit of therapeutic level (95 ng/ml) but below the toxic concentration (190 ng/ml).

A total of 79 osteoporotic patients have received orally administered slow-release sodium fluoride over a mean period of 14.9 months. The only gastrointestinal side effects were diarrhea in 2.5%, Abdominal pain and cramp in 1.3%, and nausea in 2.5%, and the only rheumatic complications were mild foot pain in 2.5% and joint pain in 3.8% of patients (Pak et al., *Am. J. Bone Min. Res.*, Vol. 3, pp 563–571 (1986)). These figures are much lower than those reported with enteric-coated or plain preparations of sodium fluoride (see Table 1). Thus, the present invention minimizes gastrointestinal hazards by limiting the amount of fluoride released to form corrosive hydrofluoric acid in the stomach. It also reduces rheumatic complications by preventing toxic levels of fluoride from being reached in blood, thus averting chances for the development of fluorosis.

Additional studies were conducted to determine if the maintenance of serum fluoride level within the therapeutic window has a desired beneficial effect on bone in osteoporosis. Serum osteocalcin is believed to be a marker for bone forming activity (Zerwekh et al., J. Clin. Endocr. Metab., Vol. 60, 1985, pp. 615–617). During long-term intermittent therapy with slow-release sodium fluoride (3 months out of every 5 months), serum osteocalcin progressively rose, (Pak et al., *Am. J. Bone Min. Res.*, Vol. 1, pp 563–571 (1986)). Thus, the rise in serum fluoride to the therapeutic level is exerting appropriate physiological action on bone.

In 21 patients with osteoporosis and receiving orally administered sodium fluoride (slow-release formulation) intermittently (3 months out of every 5 months) at a dose of 25 mg twice/day, spinal bone density was measured by dual photon absorptiometry. The bone density progressively increased (+8.3% over 3 years). Their fracture (all sites) rate declined from 1.65 (patient year before treatment to 0.16/patient on treatment ($p<0.001$)). Bone biopsy showed increased amount of normally mineralized bond after treatment.

In 20 patients with osteoporosis recovery slow-release NaF (25 mg twice/day) continuously for 12 months with 1 month withdrawal between yearly treatment periods, spinal bone density rose significantly by 9% over 1.5 years. Their fracture rate declined from 3.26/patient year to 0.09/patient year ($p<0.001$). Thus, the slow-release sodium fluoride formulation of the present invention appears to be effective in making more bone and in averting new fractures.

The following examples are included to further describe preferred embodiments of the present invention and are not intended to limit the invention unless otherwise specifically indicated in the claims appended hereto.

EXAMPLE 1

In Vitro Fluoride Release is Delayed By Talc

Five tablet preparations comprising sodium fluoride were made by the methods described earlier herein. Each tablet preparation contained carnauba wax, 25 mg of sodium fluoride and 4 mg of magnesium stearate. Tablet preparations 1–3 were devoid of talc, preparation 4 was devoid of talc and compressible sugar and preparation 5 contained talc. Table 3 shows the composition of preparations 1–5.

TABLE 3

Composition of Tablet Preparations

| Composition (mg/tablet) | Preparation | | | | |
|---|---|---|---|---|---|
| | 1 | 2 | 3 | 4 | 5 |
| Carnauba Wax | 125 | 125 | 100 | 100 | 100 |
| Sodium Fluoride | 25 | 25 | 25 | 25 | 25 |
| Magnesium Stearate | 4 | 4 | 4 | 4 | 4 |
| Compressible Sugar | 45 | 65 | 90 | — | 90 |
| Talc | — | — | — | — | 11 |

In vitro release of fluoride was determined from these 5 preparations (Table 4 and FIG. 1). All preparations without talc (preparations 1–4) showed a rapid fluoride release of 55–62% in 2 hours and 85–93% in 5 hours. The absence of compressible sugar did not significantly alter the dissolution characteristic, as indicated by similar fluoride release between preparation 4 and preparation 3.

However, the presence of a small amount of talc significantly retarded the rate of in vitro dissolution. Thus, the fluoride release from preparation 5 was only 42.5% in 2 hours and only 61.9% in 5 hours.

TABLE 4

In Vitro Release of Fluoride

| | In Vitro Dissolution (%) of Preparation | | | | |
|---|---|---|---|---|---|
| Time | 1 | 2 | 3 | 4 | 5 |
| 1 hr. | 48.3 | 46.5 | 45.3 | 45.5 | 31.4 |
| 2 hrs | 60.5 | 55.3 | 54.5 | 62.3 | 42.5 |
| 3 hrs | 79.8 | 69.1 | 66.8 | 70.6 | 46.9 |
| 4 hrs | 87.0 | 80.2 | 78.5 | 81.4 | 55.0 |
| 5 hrs | 93.2 | 90.1 | 88.2 | 85.4 | 61.9 |

TABLE 4-continued

In Vitro Release of Fluoride

| | In Vitro Dissolution (%) of Preparation | | | | |
|---|---|---|---|---|---|
| Time | 1 | 2 | 3 | 4 | 5 |
| 6 hrs | | 95.8 | | 88.3 | 70.8 |
| 7 hrs | | | | 90.5 | |
| 8 hrs | | | | 96.6 | 93.4 |

EXAMPLE 2

Intestinal Absorption of Fluoride is Delayed by Talc in the NaF Preparation

In six normal subjects, a fluoride bioavailability study was performed after they ingested 50 mg of preparation 4 (NaF without talc, as shown in Example 1) on one occasion, and 50 mg of preparation 5 (NaF with talc) on another occasion. Serum fluoride level rose more slowly and declined less rapidly following oral administration of preparation 5, which also had a slower in vitro release (FIG. 2). This result illustrates both the relationship of in vitro and in vivo characteristics and the essentiality of talc.

It was further found that the in vivo slow-release fluoride data presented in the Hasvold and Ekren reference, cited earlier herein, was closely analogous to that obtained with the talc-free tablet of preparation 4.

The serum fluoride levels of two individual patients who had ingested 50 mg NaF in a tablet (preparation 5) of the present invention (with talc) or in a talc-free tablet (preparation 4) are shown in Table 5.

TABLE 5

Serum Fluoride Level Following a Single Oral Dose of Slow-Release NaF with Talc and without Talc

| | Serum Fluoride, ng/ml | | | |
|---|---|---|---|---|
| Time, hr | Case J.H. | | Case D.T. | |
| following NaF (50 mg) Administration | With Talc | Without Talc | With Talc | Without Talc |
| 0 | 25.3 | 48.3 | 35.1 | 21.1 |
| 0.5 | 45.2 | 163.6 | 41.6 | 576.3 |
| 1 | 66.0 | 163.6 | 73.4 | 473.4 |
| 2 | 116.6 | 124.2 | 117.2 | 102.0 |
| 3 | 116.6 | 106.1 | 79.9 | 94.3 |
| 5 | 73.2 | 94.3 | 58.6 | 98.1 |
| 7 | 73.2 | 66.1 | 44.2 | — |
| 10 | 59.7 | 68.8 | 54.4 | 110.3 |
| 12 | 54.3 | 63.6 | 45.4 | — |

EXAMPLE 3

Sodium Fluoride Bioavailability

In 8 normal volunteers, serum fluoride was measured at various times during the 24 hours following an oral administration of 25 mg each of slow-release sodium fluoride, plain (rapid release) sodium fluoride or placebo (without fluoride).

There was no significant change in serum fluoride following placebo administration (Pak et al., *Am. J. Bone Min. Res.*, Vol. 1, pp 563–571 (1986)). FIG. 3 shows fluoride bioavailability in 8 normal subjects who had not been on sodium fluoride treatment. The arrow indicates the time when a single dose of placebo, plain sodium fluoride (25 mg), or slow-release sodium fluoride (25 mg) was administered orally. The significant difference from the placebo phase is shown by * for $p<0.05$. Mean and SEM are shown. Serum fluoride reached a high level rapidly following administration of plain sodium fluoride. However, there was a more gradual rise in serum fluoride, with avoidance of such a high rapidly occurring peak of serum fluoride, following administration of sodium fluoride in the slow-release form. Twelve hours after slow-release sodium fluoride administration, serum fluoride level was significantly higher than in the basal state (placebo level).

Thus, a sustained elevation in serum fluoride level, with avoidance of high peaks, could be achieved with the slow-release sodium fluoride preparation of the present invention. The more gradual rise in serum fluoride level with the slow-release preparation suggests that the fluoride ion is only slowly released into gastric juice.

EXAMPLE 4

Maintenance of Serum Fluoride Within Therapeutic Window During Long-Term Slow-Release Sodium Fluoride Therapy In 37 patients with osteoporosis, slow-release sodium fluoride was given orally at a dosage of 25 mg twice/day for 3 months out of every 5 month cycle (Pak et al., Am. J. Bone Min. Res., Vol. 1, pp 563-571 (1986)).

Serum fluoride level rose significantly during treatment as seen in FIG. 4. FIG. 4 shows fasting serum fluoride following long-term intermittent sodium fluoride (slow-release) therapy. Sodium fluoride was given for 3 months in each 5-month cycle. The shaded area represents "therapeutic window," enclosing threshold therapeutic level and threshold toxic concentration of fluoride in serum. (•) Values derived during sodium fluoride treatment; (o) values obtained before or after stopping sodium fluoride treatment. The significant difference from the pretreatment value is indicated by * for $p<0.05$. The treated values were above the lower limit of therapeutic range (95 ng/ml) and below the potentially toxic level (190 ng/ml). It is generally believed that serum level of at least 95 ng/ml must be reached to exert beneficial effect on bone, and that toxic systemic side effects (e.g. rheumatic symptoms) may appear when serum fluoride level exceeds 190 ng/ml.

Thus, long-term use of the slow-release sodium fluoride formulation of the present invention provided a sustained maintenance of therapeutic but safe levels of serum fluoride.

EXAMPLE 5

Adverse Reactions to Slow-Release Sodium Fluoride

Seventy-nine osteoporotic patients received slow-release sodium fluoride for a cumulative period of 1,177 months. Adverse reactions were uncommon and minor (Table 6) (Pak et al., Am. J. Bone Min. Res., Vol. 1, pp 563-571 (1986)).

The only gastrointestinal side effects noted were diarrhea in 2.5%, pain or cramp in 1.3% and nausea in 2.5% of patients. Although two patients had positive test for occult blood in stool, the origin of blood loss was due to hemorrhoids in one and dental extraction in the other. Two patients (2.5%) had plantar fascitis and three (3.8%) had synovitis which resolved upon reduction of sodium fluoride dosage. In contrast, other workers reported a much higher incidence of gastrointestinal and rheumatic complications using non-slow-release sodium fluoride preparations (Table 1).

The reduced gastrointestinal side effects observed with the use of slow-release sodium fluoride could be explained by the avoidance of the excessive gastric formation of corrosive hydrofluoric acid due to the slow-release nature of the product essentially bypassing the stomach. The low incidence of rheumatic complication could be due to the avoidance of high levels of fluoride in serum.

TABLE 6

Side Effects of Slow-Release NaF

| Symptoms | No. Patients | % |
|---|---|---|
| Gastrointestinal | 0 | 0 |
| Vomiting | 0 | 0 |
| Belching | 0 | 0 |
| Diarrhea | 2 | 2.5 |
| Pain/cramp | 1 | 1.3 |
| Melena | 0 | 0 |
| Dyspepsia | 0 | 0 |
| Anorexia | 0 | 0 |
| Nausea | 2 | 2.5 |
| Bleeding | 0 | 0 |
| Rheumatic | | |
| Plantar fascitis | 2 | 2.5 |
| Synovitis | 3 | 3.8 |

EXAMPLE 6

Long-Term Effect of Slow-Release Sodium Fluoride Therapy on Serum Osteocalcin

Serum osteocalcin is believed to be a marker of osteoblastic (bone-forming) activity. Following administration of slow-release sodium fluoride 25 mg twice/day for 3 months out of every 5 month cycle in 18 osteoporotic patients, serum osteocalcin level obtained during treatment gradually increased (Pak et al, Am. J. Bone Min. Res., Vol. 1, pp 563-571 (1986)). FIG. 5 shows the relationship between serum osteocalcin concentration and the duration of sodium fluoride treatment. This figure depicts the mean value of serum osteocalcin from all available patients at each time period, as well as the regression line calculated from the mean values. A significant correlation was also observed when individual values from all participating patients were plotted against time ($p<0.001$).

Thus, sufficient fluoride must have been absorbed to exert its expected physiological action on bone.

EXAMPLE 7

Effect of Long-Term Slow-Release NaF Therapy on Vertebral Bone Density

In 21 patients with osteoporosis, slow-release sodium fluoride was provided at a dosage of 25 mg twice/day intermittently (3 months out of every 5 month cycle) for an average total duration of 3 years.

Figure 6:
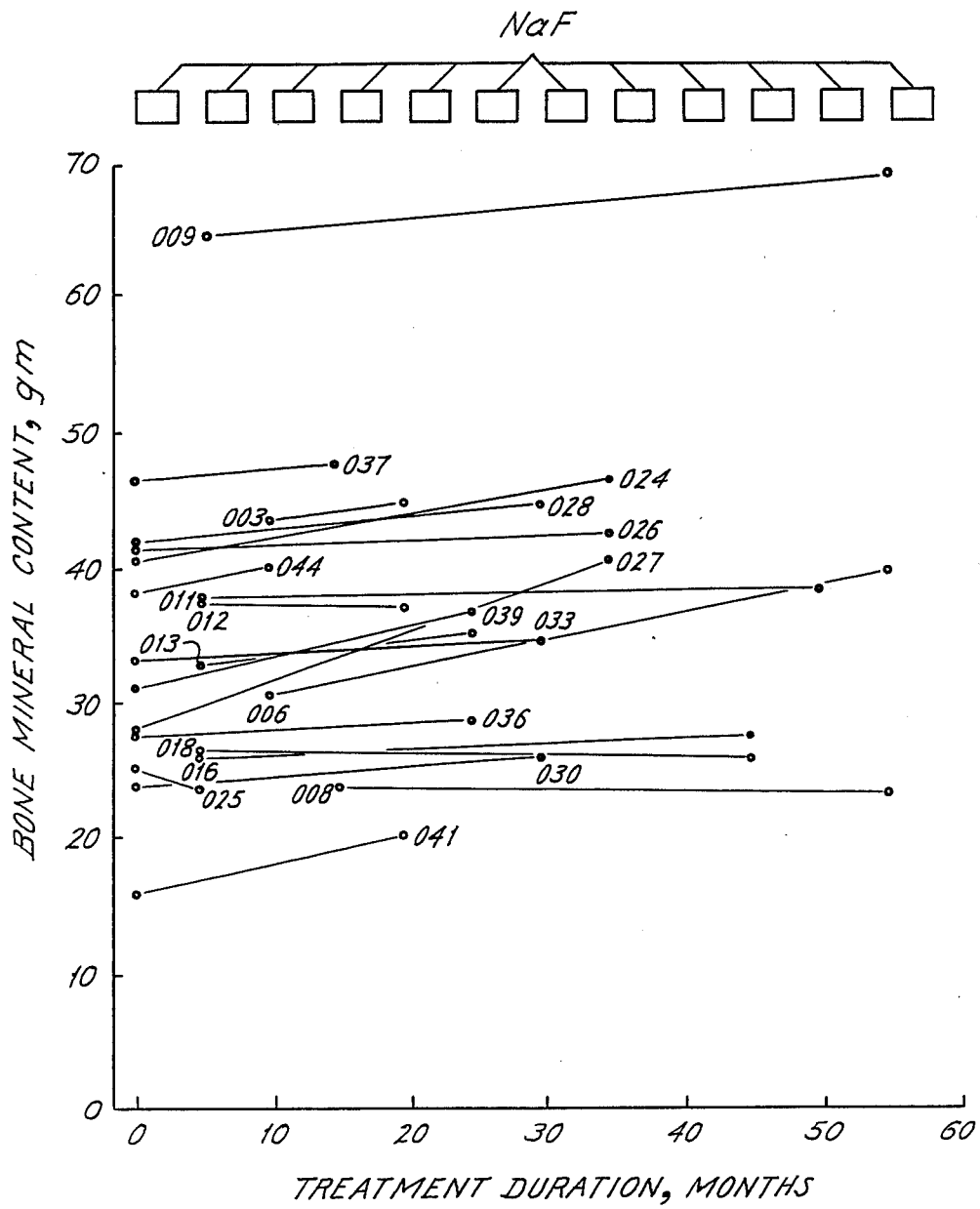
FIG. 6 shows that lumbar bone density increases in most osteoporotic patients treated with slow-release NaF.

Bone density in lumbar vertebral increased in most patients (FIG. 6). The mean change for the group was +8.3% after 3 years of treatment. Thus, sodium fluoride therapy (slow-release) may augment vertebral bone mass, whereas the expected finding without treatment would be a decline in bone density (mass).

Similarly, in 20 patients receiving slow-release NaF (25 mg twice/day) for 12 months (with a month of withdrawal between yearly treatment periods), vertebral bone density rose by 9% over 1.5 years. FIG. 6 shows the effect of slow-release NaF treatment in vertebral bone mineral content. Each line represents the first and the last measurement in the same patient.

EXAMPLE 8

Effect of Long-Term Slow-Release NaF Treatment of Skeletal Fracture

Figure 7:
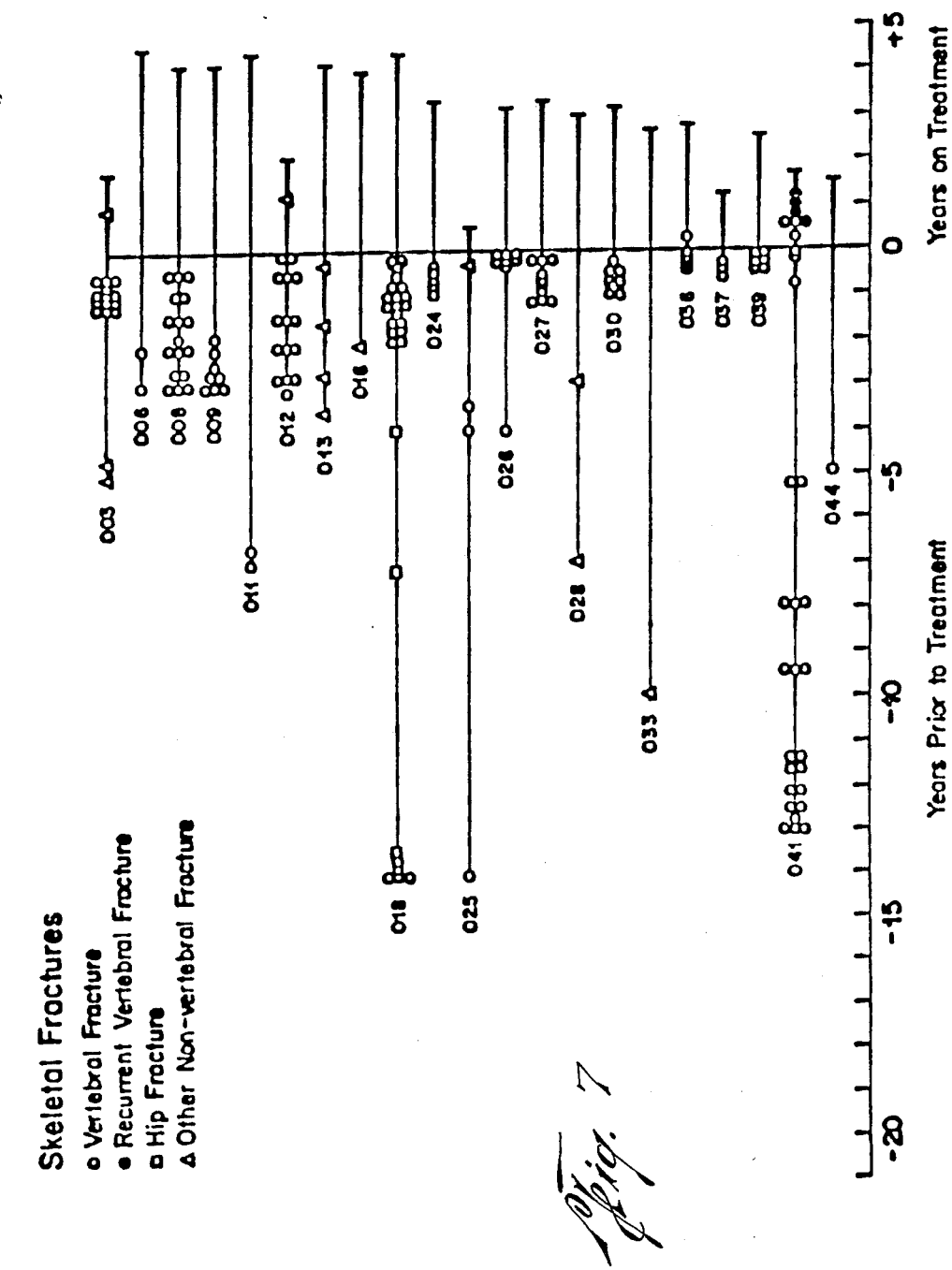
FIG. 7 shows inhibition of fractures by slow-release NaF treatment in osteoporotic patients.

Twenty-one patients received slow-release sodium fluoride 25 mg twice/day (3 months out of every 5 month cycle) for an average duration of 3 years. The fracture incidence was therefore 30–160/1000 patient-yr during treatment, much lower than the reported fracture incidence in untreated osteoporotic patients of 834/1000 patient-yr (Riggs et al., N. Engl. J, Med., Vol. 306, 1982, pp. 446–450). FIG. 7 shows the effect of long term slow-release NaF treatment on vertebral fractures. Each line represents separate patient. Each symbol indicates separate fracture episode. Closed circles show recurrent fracture on an already involved vertebra. Numbers preceding each line represent patient study codes.

Thus, slow-release sodium fluoride was effective in preventing new fractures in postmenopausal osteoporotic women.

EXAMPLE 9

Effect of Long-Term Slow-Release NaF Treatment on Bone Biopsy

Transcortical ileal bone biopsies were performed before and after 4 cycles (3 months of NaF 25 mg twice/day followed by 2 months without in each cycle) in 12 osteoporotic patients. Bone formation surface significantly increased from 1.7 to 2.3% following treatment. Mineral apposition rate rose significantly from 0.6 to 1.4 micrometers/day, as did mean wall thickness from 40 to 51 micrometers. The bone was lamellar in appearances. Thus, slow-release NaF treatment may cause formation of new, adequately mineralized bone.

Changes may be made in the formulations and procedures described herein without departing from the concept and scope of the invention as defined in the following claims.

What is claimed is:

1. A tablet adapted for slow gastrointestinal release of fluoride, the tablet comprising by weight 1% to 10% talc, 1% to 5% lubricant, 20% to 65% compressible sugar and 8% to 12% sodium fluoride dispersed substantially homogeneously throughout a carnauba wax matrix, said carnauba wax being between 35% to 70% by weight of the tablet.

2. The tablet of claim 1 wherein the lubricant is magnesium stearate.

3. The tablet of claim 1 defined further as comprising about 5% talc, about 40% compressible sugar and about 11% sodium fluoride.

4. The tablet of claim 1 defined further as comprising about 25 mg. sodium fluoride.

5. A process for maintaining an individual's serum fluoride at a therapeutic and safe level between about 95 ng/ml and about 190 ng/ml, the process comprising administering to the individual twice daily a tablet adapted for slow gastrointestinal release of fluoride, the tablet comprising talc and sodium fluoride dispersed substantially homogeneously throughout a carnauba wax matrix.

6. A process for maintaining an individual's serum fluoride at a therapeutic and safe level between about 95 ng/ml and about 190 ng/ml, the process comprising administering twice daily to the individual, a tablet adapted for slow gastrointestinal release of fluoride, the tablet comprising by weight 1% to 10% talc, and 8% to 12% sodium fluoride dispersed substantially homogeneously throughout a carnauba wax matrix, said carnauba wax being between 35% to 70% by weight of the tablet.

7. A process for maintaining an individual's serum fluoride at a therapeutic and safe level between about 95 ng/ml and about 190 ng/ml, the process comprising administering twice daily to the individual, a tablet adapted for slow gastrointestinal release of fluoride, the tablet comprising by weight 1% to 10% talc, 1% to 5% lubricant, 20% to 65% compressible sugar and 8% to 12% sodium fluoride dispersed substantially homogeneously throughout a carnauba wax matrix, said carnauba wax being between 35% to 70% by weight of the tablet.

8. The process of claim 7 wherein the lubricant is magnesium stearate.

9. The process of claim 5, 6 or 7 wherein the administration is for intermittent periods.

10. The process of claim 5, 6 or 7 wherein the tablet of claim is defined further as comprising about 5% talc, about 45% carnauba wax, about 2% magnesium stearate lubricant, about 40% compressible sugar and about 11% sodium fluoride.

11. The process of claim 5, 6 or 7 wherein the tablet comprises about 25 mg sodium fluoride.

12. A process of making more of adequately mineralized bone and inhibiting fractures, said process being accomplished by long-term maintenance of serum fluoride at a safe and therapeutic level using a slow-release preparation of sodium fluoride prepared according to claim 5, 6 or 7.

13. A tablet adapted for slow gastrointestinal release of fluoride, the tablet comprising by weight about 5% talc, about 45% carnauba wax, and about 11% sodium fluoride.

14. A method of producing a slow release sodium fluoride tablet comprising the steps of:
    (a) blending a combination comprising finely powdered carnauba wax, talc and sodium fluoride to form a mixture;
    (b) passing the mixture of step (a) through a mesh screen; and
    (c) tableting the screened mixture of step (b) to form the slow release sodium fluoride tablet.

15. A method of producing a slow release sodium fluoride tablet comprising the steps of:
    (a) measuring a quantity of finely powdered carnauba wax;
    (b) measuring a quantity of sodium fluoride, or sodium fluoride with a binder, and talc;
    (c) blending the quantity of carnauba wax with the quantity measured in step (b) to form a mixture;
    (d) passing the mixture of step (a) through a mesh screen; and
    (f) tableting the screened mixture of step (d) to form a slow release sodium fluoride tablet.

16. The method of claim 14 wherein the finely powdered carnauba wax of step (a) has the following meshed screen characteristics:

| Mesh | Percent Retained |
|------|------------------|
| 60   | 1                |
| 100  | 1                |
| 150  | 60               |

-continued

| Mesh | Percent Retained |
|---|---|
| 200 | 37 |

17. The method of claim 15 wherein the mixture of step (a) has a ratio of sodium fluoride/wax or (sodium fluoride +binder) /wax in the range of between about 1.24 and 5.9.

18. The method of claim 15 wherein the tablet is further defined by the addition of a lubricant to the mixture, and the lubricant is defined further as being magnesium stearate.

19. The method of claim 18 wherein the tablet comprises about 1-5 parts/100 magnesium stearate.

20. The method of claim 18 wherein the tablet comprises magnesium stearate further defined as passed through a 20-mesh screen.

21. The method of claim 15 wherein the binder is a compressible sugar.

22. The method of claim 21 wherein the tablet comprises about 20-65 parts/100 compressible sugar.

23. The method of claim 14 or 15 wherein the tablet sodium-fluoride, carnauba wax and talc are in the following proportions on a 100-parts-by-weight basis:

| | |
|---|---|
| sodium fluoride | 8-12 parts |
| talc | 1-10 parts |
| carnauba wax | 35-70 parts |

* * * * *

UNITED STATES PATENT AND TRADEMARK OFFICE
CERTIFICATE OF CORRECTION

PATENT NO. : 4,904,478

DATED : February 27, 1990

INVENTOR(S) : Neill B. Walsdorf and Charles Y. C. Pak

It is certified that error appears in the above-identified patent and that said Letters Patent is hereby corrected as shown below:

In claim 10, column 14, line 23, delete the term "of claim".

In claim 12, column 14, line 34, delete the term "5, 6 or 7" and substitute the term --14, 15 or 16-- therefor.

In claim 15, column 14, line 56, in step (d) delete the term "(a)" and substitute the term --(c)-- therefor.

In claim 17, column 15, line 8, delete the term "(a)" and substitute the term --(c)--therefor.

In claim 17, column 15, line 10, delete the term "1.24 and 5.9" and substitute the term --1/24 and 5/9-- therefor.

Signed and Sealed this

Twenty-sixth Day of November, 1991

*Attest:*

HARRY F. MANBECK, JR.

*Attesting Officer*     *Commissioner of Patents and Trademarks*